United States Patent [19]
Hamilton et al.

[11] Patent Number: 5,435,993
[45] Date of Patent: Jul. 25, 1995

[54] 80% VOC, SINGLE PHASE AEROSOL HAIR SPRAY COMPOSITION

[75] Inventors: Brenda Hamilton, Parsippany; Edward W. Walls, Jr., Cranford, both of N.J.

[73] Assignee: ISP Investments Inc., Wilmington, Del.

[21] Appl. No.: 276,135

[22] Filed: Jul. 18, 1994

[51] Int. Cl.$^6$ .............................................. A61K 7/11
[52] U.S. Cl. ................................... 424/47; 424/45; 424/401; 424/DIG. 1; 424/DIG. 2; 424/70.1; 424/70.2; 424/70.11
[58] Field of Search .................... 424/45, 47, DIG. 1, 424/DIG. 2, 401, 70, 71, 70.1, 70.2, 70.11

[56] References Cited

U.S. PATENT DOCUMENTS

| | | | |
|---|---|---|---|
| 4,164,562 | 8/1979 | Nandagiri | 424/47 |
| 5,176,898 | 1/1993 | Goldberg | 424/47 |
| 5,196,495 | 3/1993 | Chuang | 526/264 |

OTHER PUBLICATIONS

Brookins, J. Soc. Cosmetic Chemists 16, 309, 1965.

*Primary Examiner*—Gollamudi S. Kishore
*Attorney, Agent, or Firm*—Walter Katz; Marilyn J. Maue; Joshua J. Ward

[57] ABSTRACT

An 80% VOC, single phase aerosol hair spray composition based on greater than 15% hydrocarbons as propellant is described. The composition includes a predetermined small amount of dimethyl ether as cosolvent to assure solubilization of the hair fixative resin, alcohol, water and hydrocarbon components of the composition within a single phase.

6 Claims, No Drawings

80% VOC, SINGLE PHASE AEROSOL HAIR SPRAY COMPOSITION

BACKGROUND OF THE INVENTION

1. Field of the Invention

This invention relates to an 80% VOC (Volatile Organic Compound), single phase aerosol hair spray composition, and, more particularly, to a hair spray composition based upon greater than 15% hydrocarbon as propellant having advantageous spray characteristics and acceptable user performance.

2. Description of the Prior Art

Aerosol hair sprays based on alcohol as the solvent for a hair fixative resin have employed hydrocarbons such as propane and butane as the propellant. Hydrocarbons are useful in such compositions because they are low cost and also because they can be used in economical unlined tin plate cans. However, recent governmental legislation has required that hair sprays contain less ethanol and/or propellant, which are the volatile organic constituents in the composition. For example, to meet an 80% VOC standard, it is necessary that the ethanol and propellant components comprise no more than 80% by weight of the composition. However, hydrocarbons are less soluble in such a high water content composition; in fact, in a water-hydrocarbon system containing more than 15% hydrocarbon, the composition separates into 2 phases, an aqueous phase and a hydrocarbon phase. Furthermore, the increased water content in the composition may cause can corrosion problems. For these reasons, dimethyl ether has been suggested as a replacement for hydrocarbon propellants. Dimethyl ether is advantageous as a propellant because it is soluble up to 35% in water. However, dimethyl ether is costly and also it does not alleviate the potential problem with can corrosion. In fact, DME may dissolve the rubber gasketing present in the valve of the actuator mechanism.

The state of the prior art in this field is represented by the following patents:

Martino, in U.S. Pat. No. 5,021,238, described a 2-phase aerosol hair spray composition having a dimethyl ether-to-water weight ratio of greater than 0.5:1. This composition, however, required shaking before use to form a semi-stable emulsion.

Shepard, in U.S. Pat. No. 3,137,416, described a 3-phase aerosol system for dispensing a hair spray resin comprising a gaseous propellant, a liquid propellant and an aqueous liquid.

Presant, in U.S. Pat. No. 3,207,386 described a 2-phase system for dispensing a liquid from a container under pressure by means of vaporization of a propellant within the container. The system comprised a propellant as the vapor phase and an essentially continuous liquid as the aqueous phase, and further included an active ingredient as solute, water as solvent and dimethyl ether as propellant. No hydrocarbon propellants were present, however, in this system.

Clapp, in U.S. Pat. No. 2,995,278, described a package for dispensing an aerosol spray composition which was present in the form of both aqueous and non-aqueous phases. The non-aqueous phase included both a hydrocarbon and a liquified halogen-substituted hydrocarbon as propellants. Dimethyl ether was not present in this composition.

Other patents in this field include U.S. Pat. Nos. 4,134,968; 4,874,604; 4,933,170; 5,176,898; 4,923,695; 4,315,910; and 5,266,303.

Accordingly, it is an object of this invention to provide an 80% VOC, single phase aerosol hair spray composition based upon an amount greater than 15% of hydrocarbon as the propellant.

Another object of this invention is to provide an 80% VOC, single phase aerosol hair spray composition having 15.1 to 20% hydrocarbon as propellant and 0.5 to 5% dimethyl ether as solubilizer for all the components of the composition.

Still another object herein is to provide such a hair spray composition having advantageous spray patterns and user performance.

These and other objects and features of the invention will be made apparent from the following description of the invention.

SUMMARY OF THE INVENTION

An 80% VOC, single phase aerosol hair spray composition is described herein using greater than 15% of one or more hydrocarbons as the propellant. The hair spray formulation herein includes a predetermined amount of a hair fixative polymer, and defined proportions of alcohol, water and the hydrocarbon propellant. A small amount of dimethyl ether is present as a cosolvent to solubilize all the components of the composition within a single phase.

The composition exhibits advantageous spray characteristics and acceptable user performance, while enabling a variety of low cost aerosol can and packaging options.

DETAILED DESCRIPTION OF THE INVENTION

The 80% VOC, single phase aerosol hair spray composition of the invention comprises, by weight:

(a) 1.5–7% of a hair fixative polymer, optionally neutralized up to 100 mole %,
(b) 54.5–69.5% of ethanol,
(c) 10–18.5% of water,
(d) 15.1–20% of a hydrocarbon propellant, or mixtures thereof, and
(e) 0.5–5% of dimethyl ether.

A preferred hair spray composition of the invention comprises:

(a) 4–5% of a hair fixative polymer, optionally neutralized to an extent of about 10–25 mole %,
(b) about 58–63.5% of ethanol,
(c) about 15–16% of water,
(d) about 16–17% of hydrocarbon propellant, and
(e) about 1–3.5% of dimethyl ether.

(a) Hair Fixative Polymer

The following hair fixative polymers are useful in the composition of the invention.

TABLE 1

| Resin Trade Names [Supplier] | CTFA Designations |
|---|---|
| Gantrez ® ES-225 [ISP] | Ethyl ester of PVM/MA copolymer |
| Gantrez ® V-225 [ISP] | |
| Gantrez ® ES-425 [ISP] | Butyl ester of PVM/MA copolymer |
| Gantrez ® V-225 [ISP] | |
| Gaffix VC-713 [ISP] | Vinyl caprolactam/ PVP/ dimethyl aminoethyl methacrylate copolymer |
| PVP K-30 [ISP] | PVP |
| PVP/VA E-335 [ISP] | PVP/Vinyl Acetate Copolymer |
| PVP/VA E-735 [ISP] | PVP/Vinyl Acetate Copolymer |
| Amphomer ® [NSC]* | Octylacrylamide/acrylates/ |

TABLE 1-continued

| Resin Trade Names [Supplier] | CTFA Designations |
|---|---|
| Resyn ® 28-2310 [NSC] | butylaminoethyl methacrylate copolymer Vinyl acetate/crotonic acid copolymer |
| Resyn ® 28-2930 [NSC] | Vinyl acetate/crotonic acid/vinyl neodecanoate copolymer |
| Vertalyl ™ 40 [NSC] | Octylacrylamide/acrylates copolymer |
| Vertalyl ™ 42 [NSC] | Octylacrylamide/acrylates copolymer |
| Ultrahold ™ [BASF] | Acrylate/acrylamide copolymer |
| Luviset CAP ™ [BASF] | Vinyl acetate/crotonic acid/vinyl propionate copolymer |
| Dermacryl ™ 79 [NSC] | Acrylates/t-octylpropenamide copolymer |
| Lovocryl ™ [NSC] | Octylacrylamide/acrylates copolymer-2 |

*NSC - National Starch and Chemical Corporation

Preferred hair fixative polymers for use herein include Gantrez® ES-425 and Gantrez® V-425, which are the butyl half-ester of maleic anhydride and methyl vinyl ether, and which is supplied by ISP as an ethanolic solution containing 50% by weight of the polymer.

A suitable amount of a hair fixative polymer, on a solids basis, is about 1.5-7% by weight, preferably 4-5%.

The polymer optionally may be neutralized up to 100 mole %, preferably 10-25%, by alkaline agents such as 2-amino-2-methyl-1-propanol (AMP), KOH, NaOH or $NH_4OH$ blends thereof, and the like.

(b) Ethanol

The ethanol component of the composition suitably is present in a predetermined amount of 54.5 to 69.7% of the composition, preferably 58 to 63.5%.

(c) Water

The water component of the composition suitably is present in an amount of 10-18.5% of the composition, preferably 15-16%.

The total amount of polymer, water and other non-volatile components in the composition is 19-21%, preferably 20%.

(d) Hydrocarbon Propellants

Suitable hydrocarbons for use herein include propane and butane, both as the normal and isomeric forms thereof. A single hydrocarbon or mixtures thereof may be used. Preferably the hydrocarbon is a predetermined mixture of propane and iso-butane.

The amount of hydrocarbon present herein is in excess of its normal solubility limit in water of 15%. Suitably such amount is 15.1-20%, preferably 16-17%.

(e) Dimethyl Ether (DME)

DME functions herein as a cosolvent to solubilize all the components of the composition within a single phase. In this invention, a small amount, suitably 0.5-5%, and preferably 1-3.5%, of dimethyl ether will perform such function without significantly increasing the likelihood of can corrosion during use.

In summary, the hair spray composition of the invention includes:
(a)+(c)=19-21%
(d)+(e)=15.6-25%
(b)+(d)+(e)=80%

Tables 2 and 3 below will illustrate the invention more particularly with respect to specific working examples and spray characteristics thereof.

TABLE 2

(COMPOSITIONS)

| COMPONENT | EXAMPLE NO. | | | | | | |
|---|---|---|---|---|---|---|---|
| | 1 | 2 | 3 | 4 | 5 | 6 | 7 |
| Gantrez ® ES-425 | 8.00 | 8.00 | 8.00 | 8.00 | — | — | — |
| Gantrez ® V-425 | — | — | — | — | 8.00 | 8.00 | 8.00 |
| AMP-95 | 0.23 | 0.36 | 0.23 | 0.36 | 0.23 | 0.23 | 0.23 |
| Ethanol, SDA-40 | 56.00 | 56.00 | 59.00 | 59.00 | 59.00 | 59.00 | 59.00 |
| Water, D.I. | 15.77 | 15.64 | 15.77 | 15.64 | 15.77 | 15.77 | 15.67 |
| A-108, propane | 10.00 | 10.00 | 10.00 | 10.00 | 10.00 | 10.00 | 8.50 |
| A-17, butane | 7.00 | 7.00 | 3.50 | 3.50 | — | — | — |
| A-31, isobutane | — | — | — | — | 3.50 | 6.00 | 6.00 |
| DME, dimethyl ether | 3.00 | 3.00 | 3.50 | 3.50 | 3.50 | 1.00 | 1.00 |
| | 100.00% | 100.00% | 100.00% | 100.00% | 100.00% | 100.00% | 100.00% |

AMP-95 @ 0.23% = 14 mole % neutralization
AMP-95 @ 0.36% = 22 mole % neutralization

TABLE 3

(SPRAY TEST RESULTS)

| COMPONENT | EXAMPLE NO. | | | | | | |
|---|---|---|---|---|---|---|---|
| | 1 | 2 | 3 | 4 | 5 | 6 | 7 |
| Phase (single) | Yes | Yes | Yes | Yes | Yes | Yes | No |
| Vapor Press. (psi) | 68 | 64 | 72 | 70 | 68 | 67 | — |
| Cloud Point (°F.) | 48 | 36 | 0 | -20 | — | — | — |
| Particle Size, μ | 68.85 | 67.55 | 56.51 | 63.13 | 46.91 | 51.61 | — |
| % Evacuation | 91.3 | 96.9 | 98.0 | 96.4 | 99.2 | 88.2 | — |

Valve used - Seaquist ST-71 .013" × .042"
Vapor Tap - .013"; Dip Tube - .122"
Actuator ST-100 Misty .018"

Tables 2 and 3 demonstrate that the presence of small amounts of DME in the composition of the invention at hydrocarbon levels above 15% provide a single phase system (Examples 1-6); whereas the absence of DME at the same hydrocarbon level produces a two-phase system (Example 7). Furthermore, the spray characteristics of the single phase systems of the invention are advantageous for a commercial hair spray and indicative of acceptable user performance with respect to such critical parameters as the drying time.

While the invention has been described with particular reference to certain embodiments thereof, it will be understood that changes and modifications may be made which are within the skill of the art. Accordingly, it is intended to be bound only by the following claims, in which:

What is claimed is:

1. An 80% volatile organic compound, single phase aerosol hair spray composition comprising, by weight:
    (a) 1.5-7% of a hair fixative polymer, optionally neutralized up to 100 mole %, (b) 54.5–69.5% of ethanol,
(c) 10–18.5% of water,
(d) 15.1–20% of a hydrocarbon propellant, or mixtures thereof, and
(e) 0.5–5% of dimethyl ether,
wherein (a)+(c)=19–21%; (d)+(e)=15.6–25% and (b)+(d)+(e)=80%.

2. An 80% volatile organic compound, single phase aerosol hair spray composition according to claim 1 wherein:
(a) is 4–5%, optionally neutralized to 10–25%,
(b) is 58–63.5%,
(c) is 15–16%,
(d) is 16–17% and
(e) is 1–3.5%.

3. An aerosol hair spray composition according to claim 1 wherein (a) is the butyl half-ester of the copolymer of maleic anhydride and methyl vinyl ether.

4. A composition according to claim 3 wherein (a) is neutralized to 10–25%.

5. A composition according to claim 1 wherein (d) is a mixture of propane and butane.

6. A composition according to claim 5 wherein (d) is a mixture of 6–10% propane and 1.5–6% butane.

* * * * *